US009067002B2

(12) United States Patent
Trollsas et al.

(10) Patent No.: US 9,067,002 B2
(45) Date of Patent: *Jun. 30, 2015

(54) TAILORED ALIPHATIC POLYESTERS FOR STENT COATINGS

(71) Applicant: Abbott Cardiovascular Systems Inc., Santa Clara, CA (US)

(72) Inventors: O. Mikael Trollsas, San Jose, CA (US); Lothar W. Kleiner, Los Altos, CA (US); Syed F. A. Hossainy, Hayward, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/185,699

(22) Filed: Feb. 20, 2014

(65) Prior Publication Data

US 2014/0186417 A1    Jul. 3, 2014

Related U.S. Application Data

(63) Continuation of application No. 11/827,783, filed on Jul. 13, 2007, now Pat. No. 8,685,430.

(60) Provisional application No. 60/830,823, filed on Jul. 14, 2006.

(51) Int. Cl.
| | |
|---|---|
| A61F 2/00 | (2006.01) |
| A61L 31/10 | (2006.01) |
| A61L 27/34 | (2006.01) |
| A61L 31/14 | (2006.01) |
| A61L 31/16 | (2006.01) |

(52) U.S. Cl.
CPC .................. *A61L 31/10* (2013.01); *A61L 27/34* (2013.01); *A61L 31/148* (2013.01); *A61L 31/16* (2013.01); *A61L 2300/416* (2013.01); *A61L 2400/18* (2013.01); *A61L 2420/08* (2013.01)

(58) Field of Classification Search
CPC ....... A61L 27/34; A61L 31/10; A61L 31/148; A61L 2300/416; A61L 2400/18; A61L 2420/08; A61L 31/16; C08L 67/04
USPC ................................................. 424/425, 423
See application file for complete search history.

(56) References Cited

U.S. PATENT DOCUMENTS

| | | |
|---|---|---|
| 4,320,753 A | 3/1982 | Lenz et al. |
| 4,331,697 A | 5/1982 | Kudo et al. |
| 4,563,182 A | 1/1986 | Stoy et al. |
| 5,023,316 A | 6/1991 | Benvenuti et al. |

(Continued)

FOREIGN PATENT DOCUMENTS

| | | |
|---|---|---|
| EP | 0947205 | 10/1999 |
| WO | WO 02/067908 | 9/2002 |

(Continued)

OTHER PUBLICATIONS

Durrani et al., "Biomembranes as models for polymer surfaces", Biomaterials vol. 7, pp. 121-125 (1986).

(Continued)

*Primary Examiner* — Aradhana Sasan
(74) *Attorney, Agent, or Firm* — Squire Patton Boggs (US) LLP

(57) ABSTRACT

An aliphatic polyester polymer for stent coating is described.

24 Claims, 1 Drawing Sheet

(56) References Cited

U.S. PATENT DOCUMENTS

| | | | |
|---|---|---|---|
| 5,064,817 | A | 11/1991 | Yedgar et al. |
| 5,221,711 | A | 6/1993 | Heinzman et al. |
| 5,302,385 | A | 4/1994 | Khan et al. |
| 5,455,040 | A | 10/1995 | Marchant |
| 5,527,337 | A | 6/1996 | Stack et al. |
| 5,575,818 | A | 11/1996 | Pinchuk |
| 5,744,153 | A | 4/1998 | Yewey et al. |
| 5,869,127 | A | 2/1999 | Zhong |
| 6,099,563 | A | 8/2000 | Zhong |
| 6,179,817 | B1 | 1/2001 | Zhong |
| 6,197,043 | B1 | 3/2001 | Davidson |
| 6,197,051 | B1 | 3/2001 | Zhong |
| 6,231,590 | B1 | 5/2001 | Slaikeu et al. |
| 6,270,788 | B1 | 8/2001 | Koulik et al. |
| 6,273,913 | B1 | 8/2001 | Wright et al. |
| 6,383,215 | B1 | 5/2002 | Sass |
| 6,451,050 | B1 | 9/2002 | Rudakov et al. |
| 6,497,729 | B1 | 12/2002 | Moussy et al. |
| 7,094,256 | B1 | 8/2006 | Shah et al. |
| 7,316,710 | B1 | 1/2008 | Cheng et al. |
| 7,396,541 | B2 | 7/2008 | Hossainy et al. |
| 7,722,894 | B2 | 5/2010 | Wang et al. |
| 8,685,430 | B1 | 4/2014 | Trollsas et al. |
| 2001/0029351 | A1 | 10/2001 | Falotico et al. |
| 2001/0044651 | A1 | 11/2001 | Steinke et al. |
| 2003/0021762 | A1 | 1/2003 | Luthra et al. |
| 2003/0175408 | A1 | 9/2003 | Timm et al. |
| 2003/0208258 | A1 | 11/2003 | Reilly et al. |
| 2003/0216534 | A1 | 11/2003 | Chaikof et al. |
| 2004/0018228 | A1 | 1/2004 | Fischell et al. |
| 2004/0096476 | A1 | 5/2004 | Uhrich et al. |
| 2004/0151764 | A1 | 8/2004 | Zamora |
| 2004/0180039 | A1 | 9/2004 | Toner et al. |
| 2004/0215335 | A1 | 10/2004 | Brin et al. |
| 2005/0032826 | A1 | 2/2005 | Mollison et al. |
| 2005/0058768 | A1 | 3/2005 | Teichman |
| 2005/0171596 | A1 | 8/2005 | Furst et al. |
| 2005/0208093 | A1* | 9/2005 | Glauser et al. ............ 424/423 |
| 2007/0005130 | A1 | 1/2007 | Glauser et al. |
| 2007/0020312 | A1 | 1/2007 | DesNoyer et al. |
| 2007/0110777 | A1 | 5/2007 | Joabsson et al. |
| 2008/0108824 | A1 | 5/2008 | Isch et al. |
| 2009/0030505 | A1 | 1/2009 | Kleiner et al. |
| 2011/0195263 | A1 | 8/2011 | Malotky et al. |

FOREIGN PATENT DOCUMENTS

| | | |
|---|---|---|
| WO | WO 2004/021976 | 3/2004 |
| WO | WO 2005/081752 | 9/2005 |

OTHER PUBLICATIONS

Francois et al., "Physical and biological effects of a surface coating procedure on polyurethane catheters", Biomaterials 17, pp. 667-678 (1996).

Gautier et al., Amphiphilic copolymers of ε-caprolactone and γ-substituted ε-caprolactone. Synthesis and functionalization of poly(D,L-lactide) nanoparticles, J. Biomater. Sci. Polymer Edn. vol. 14, No. 1, pp. 63-85 (2003).

Gisselfält et al., "Effect of Soft Segment Length and Chain Extender Structure on Phase Separation and Morphology in Poly(urethane urea)s", Macromol. Mater Eng. No. 3, pp. 265-271 (2003).

Lamberg et al., "Glycosaminoglycans. A biochemical and clinical review", J. of Investigative Dermatology 63, pp. 433-449 (1974).

Lee et al., "Synthesis and Degradation of End-Group-Functionalized Polylactide", J. of Polymer Science, Polymer Chem. vol. 39, pp. 973-985 (2001).

Park et al., "Blood compatibility of SPU U-PEO- heparin graft copolymers", J. of Biomedical Mat. Res. vol. 26, pp. 739-756 (1992).

Ruiz et al., "Phosphorylcholine-containing polyurethanes for the control of protein adsorption and cell attachment via photoimmobilized laminin oligopeptides", J. Biomater. Sci. Polym. Ed. 10(9), pp. 931-955 (1999).

U.S. Appl. No. 10/807,362, filed Mar. 22, 2004, Glauser et al.

U.S. Appl. No. 12/397,154, filed Mar. 3, 2009, Ludwig et al.

Coulembier et al., "New Amphiphilic Poly[(R,S)-b-malic acid-b-ε-caprolactone] Diblock Copolymers by Combining Anionic and Coordination-Insertion Ring-Opening Polymerization", Macromolecules 35, pp. 9896-9903 (2002).

Dawes, "Polyhydroxybutyrate: an Intriguing Biopolymer", Bioscience Reports 8, No. 6, pp. 537-547 (1988).

He B. et al. "Synthesis and cell affinity of functionalized poly(L-lactide-co-beta-malic acid) with high molecular weight" Biomaterials vol. 25, No. 22, pp. 5239-5247 (2004).

Jee et al., "Heparin Conjugated Polylactide as a Blood Compatible Material", Biomacromolecules 2004 5, pp. 1877-1881.

Jiyeon Choi et al., "Surface immobilization of biocompatible phospholipid polymer multilayered hydrogel on titanium alloy", Colloids and Surfaces B: Biointrefaces vol. 67, No. 2, pp. 216-223 (2008).

Lewis, A. et al., "Phosphorylcholine-based polymer coatings for stent drug delivery", Journal of Materials Science: Materials in Medicine 12, pp. 865-870 (2001).

Lewis, "Phosphorylcholine-based polymers and their use in the prevention of biofouling", Colloids and Surfaces B: Biointerfaces 18, pp. 261-275 (2000).

Parzuchowski et al., "Synthesis and Characterization of Polymethacrylate-Based Nitric Oxide Donors", Journal of the American Chemical Society 124, pp. 12182-12191 (2002).

Ranade et al., Styrenic block copolymers for biomaterial and drug delivery applications, Acta Biomaterialia 1, pp. 137-144 (2005).

Seifert et al., "Bioabsorbable, heparinized polymers for stent coating: in vitro studies on heparinization efficiency, maintenance of anticoagulant properties and improvements of stent haemocompatibility", Journal of Materials Science: Materials in Medicine 7 pp. 465-469 (1996).

Ye Sang-Ho et al., "Covalent surface modification of a titanium alloy with a phosphorylcholine-containing copolymer for reduced thrombogenicity in cardiovascular devices", J. of Biomedical Mat. Res. 31, 35, Part A, 40-42 vol. 91, No. 1 pp. 18-28 (2009).

Zeidler et al., "Synthesis of heterocyclic platelet activating factor analogues", Chemistry and Physics of Lipids 73, pp. 183-191 (1995).

Zielinski et al., "Thermodynamic Considerations of Triblock Copolymers with a Random Middle Block", Macromolecules 25, pp. 5957-5964 (1992).

\* cited by examiner

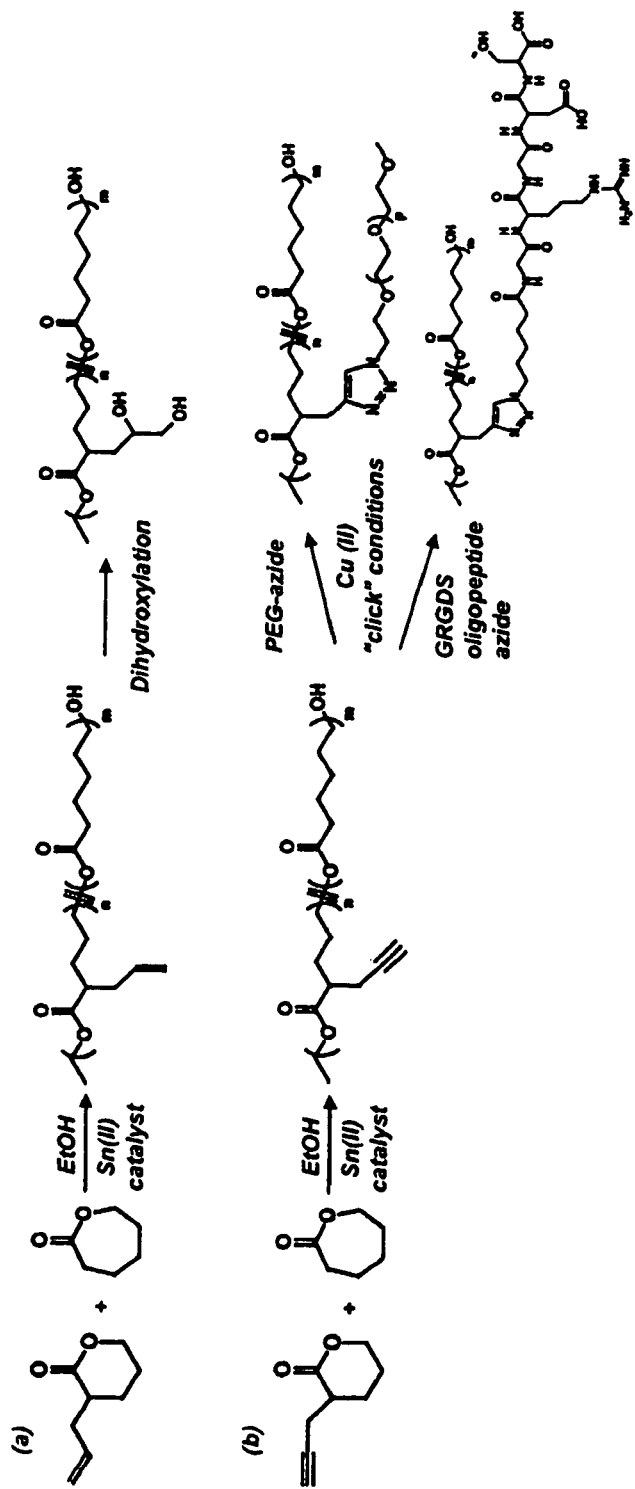

TAILORED ALIPHATIC POLYESTERS FOR STENT COATINGS

CROSS-REFERENCE TO RELATED APPLICATION

This application is a continuation of U.S. application Ser. No. 11/827,783, filed on Jul. 13, 2007, and issuing as U.S. Pat. No. 8,685,430 on Apr. 1, 2014, which claims the benefit of U.S. provisional application No. 60/830,823, filed Jul. 14, 2006, the teaching of which are both incorporated herein by reference in their entirety, and the incorporation by reference of U.S. application Ser. No. 11/827,783 expressly includes incorporation of any drawings.

FIELD OF THE INVENTION

This invention generally relates to aliphatic polyester polymers for stent coatings.

DESCRIPTION OF THE BACKGROUND

Blood vessel occlusions are commonly treated by mechanically enhancing blood flow in the affected vessels, such as by employing a stent. Stents are used not only for mechanical intervention but also as vehicles for providing biological therapy. To effect a controlled delivery of an active agent in stent medication, the stent can be coated with a biocompatible polymeric coating. The biocompatible polymeric coating can function either as a permeable layer or a carrier to allow a controlled delivery of the agent.

Although stents work well mechanically, the chronic issues of restenosis and, to a lesser extent, stent thrombosis remain. Pharmacological therapy in the form of a drug delivery stent appears to be a feasible means to tackle these issues. Polymeric coatings placed onto the stent serve to act both as the drug reservoir and to control the release of the drug. One of the commercially available polymer coated products is stents manufactured by Boston Scientific. For example, U.S. Pat. Nos. 5,869,127; 6,099,563; 6,179,817; and 6,197,051, assigned to Boston Scientific Corporation, describe various compositions for coating medical devices. These compositions provide to stents described therein an enhanced biocompatibility and may optionally include a bioactive agent. U.S. Pat. No. 6,231,590 to Scimed Life Systems, Inc., describes a coating composition, which includes a bioactive agent, a collagenous material, or a collagenous coating optionally containing or coated with other bioactive agents.

There are a very large number of biodegradable polymers for coating a stent. Aliphatic polyesters represent a particularly important example, as their biocompatible and biodegradable (resorbable) properties make them attractive for a host of applications including drug delivery vehicles, tissue engineering scaffolds, implant materials, stents and stent coatings. Commercially available aliphatic polyesters such as poly(ε-caprolactone) (PCL), polylactide (PLA), and polylactide-co-glycolide (PLGA) have proven useful in many of these applications. However, these conventional polyesters do not possess functionality. The ways to functionalize these polymers outside of the backbone ester structure are limited. As a result, the application of these polymers is limited only to applications that can be satisfied by their inherent structure.

Therefore, there is a need for polymeric materials which can be tailored to meet need of a coating on a medical device.

The polymer and methods of making the polymer disclosed herein address the above described problems.

SUMMARY OF THE INVENTION

Provided herein is a phosphorylcholine (PC) functionalized aliphatic polyester (PE). The polyester can be poly(lactic acid) (PLA), poly(lactic acid-co-glycolic acid) (PLGA), poly(glycolic acid) (PGA), polycaprolactone and their copolymers (random and block). The PC tailored polyester can be used for controlling the release of an agent. The PC part of this molecule can be exposed to the surface of this coating which is desired due to its hemocompatibility while the polyester will be buried beneath to provide for release control of a drug, if present in the coating.

In some embodiments, the polymer described herein can be used to form a coating on an implantable device, which can optionally include a bioactive agent. The bioactive agent can be any diagnostic agent, therapeutic agent, or preventive agent. Some examples of such bioactive agents include, but are not limited to, paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, dexamethasone acetate, other dexamethasone derivatives, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), TAFA-93, biolimus-7, biolimus-9, clobetasol, momethasone derivatives, pimecrolimus, imatinib mesylate, midostaurin, prodrugs thereof, co-drugs thereof, or combinations thereof. In some embodiments, the hydrophilic bioactive agent can be a peptide (e.g., RGD, cRGD or mimetics thereof), a protein (e.g., IGF, HGF, VEGF) or a drug carrying a charge.

A medical device having a coating that includes a polymer described herein can be used to treat, prevent, or ameliorate a medical condition such as atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, urethra obstruction, tumor obstruction, and combinations thereof.

BRIEF DESCRIPTION OF THE DRAWING

FIG. 1 shows the synthesis schemes for PC functionalized aliphatic polyester polymers: (a) Synthesis of 1,2-dial substituted aliphatic polyesters with tunable degradation rates and hydrophilicity; (b) synthesis of acetylene substituted aliphatic polyesters for attachment of PEG and oligopeptides by "click" cycloaddition chemistry.

DETAILED DESCRIPTION

Provided herein is a phosphorylcholine (PC) functionalize aliphatic absorbable polymers or aromatic absorbable polymers. An example of such aliphatic absorbable polymers is an aliphatic polyester. The polyester can be poly(lactic acid) (PLA), poly(lactic acid-co-glycolic acid) (PLGA), poly(glycolic acid) (PGA), polycaprolactone and their copolymers (random and block).

Some examples of aliphatic absorbable polymers include, but are not limited to, trimethylene carbonate, dioxane monomers along with LA, GA etc., poly glycerol sebacate, polyanhydrides. Some examples of aromatic absorbable polymers include, but are not limited to, polytyrosine carbonate, polyiminocarbonate, or combinations thereof.

The functionalization of PC can be both within the backbone of the polymer or as a pendant group of the polymer backbone. For example, at least one PC moiety(ies) can be incorporated in the polymer backbone or in the pendant groups of the polymer off the polymer backbone.

The PC tailored polymers described herein can be used for controlling the release of an agent. The PC part of this molecule can be exposed to the surface of this coating which is desired due to its hemocompatibility while the polyester will be buried beneath to provide for release control of a drug, if present in the coating.

In some embodiments, the polymer described herein can be used to form a coating on an implantable device, which can optionally include a bioactive agent. The bioactive agent can be any diagnostic agent, therapeutic agent, or preventive agent. Some examples of such bioactive agents include, but are not limited to, paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, dexamethasone acetate, other dexamethasone derivatives, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), TAFA-93, biolimus-7, biolimus-9, clobetasol, momethasone derivatives, pimecrolimus, imatinib mesylate, midostaurin, prodrugs thereof, co-drugs thereof, or combinations thereof. In some embodiments, the hydrophilic bioactive agent can be a peptide (e.g., RGD, cRGD or mimetics thereof), a protein (e.g., IGF, HGF, VEGF) or a drug carrying a charge.

A medical device having a coating that includes a polymer described herein can be used to treat, prevent, or ameliorate a medical condition such as atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, urethra obstruction, tumor obstruction, and combinations thereof.

Phosphorylcholine Functionalization

The synthesis of aliphatic polyesters with pendent functionality, either simple organic moieties or polymeric grafts, is key to controlling these properties. FIG. 1 (route a, upper, and route b, bottom) depicts a strategy to functionalized aliphatic polyesters (PEs). As shown in FIG. 1, functionalized lactones containing either olefins (route a) or acetylenes (route b) a to the lactone carbonyl group can be prepared, then homopolymerized, or copolymerized with unfunctionalized lactones, followed by conversion of the pendent unsaturation to the desired functionality via, e.g., dihydroxylation, reaction with PEG-azide in the presence of Cu(II) or reaction with GRGDS oligopeptide azide. The post-polymerization functionalization step requires mild conditions that allow the PE to remain intact during the course of the reaction. The flexibility offered by the approach detailed meets such requirements.

In some embodiments, the PC functionalized polymers shown in FIG. 1 can be of linear, branched, hyperbranched, dendritic, or star architecture and be functionalized at the one or more chain ends. In some embodiments, these polymers can be further modified by introducing monomers that can interact with the PC groups.

As used herein, the term PC functional refers to the attribute being modified by phosphorylcholine (PC). PC modification can be readily performed by reaction of the functional groups on the polymers disclosed herein and PC so as to attach PC to the polymer as pendant groups, for example.

In some embodiments, attaching PC to a polymer can be achieved by polymerization of a monomer including PC, with or without another monomer (see, e.g., Ruiz, L., et al., J Biomater Sci Polym Ed.; 10(9):931-55 (1999)).

In some embodiments, an alternative to the polymers structures of FIG. 1 are PE-methacrylate block copolymers and PE-acrylate block copolymers where the methacrylate and the acrylate blocks are PC functional and water-soluble and where the hydrophobic PE blocks make the structure insoluble. Under physiological conditions, once the PE blocks starts to degrade the polymer becomes more and more hydrophilic and eventually the PC block becomes water-soluble and can be cleared out.

In some embodiments, the polymer shown in FIG. 1 can be further modified to form a terpolymer with poly(ethylene glycol) (PEG), polyvinylpyrrolidone (PVP), or polyacrylamide (PAAm) as an intermediate block. Such a polymer can provide advantages of (1) good mechanical property by low $T_g$ of the intermediate block and water-sorption/plasticization and/or (2) biological non-fouling property added to the potentially pro-healing nature of PC-biomimetic property. As used herein, the term "PC-biomimetic" refers to the biological attributes similar to those of PC.

The fictionalization of PC can be both within the backbone of the polymer or as a pendant group of the polymer backbone.

Coating Design

The PC functionalized polymer described above can be used to coat a medical device with different coating design.

In some embodiments, the PC functionalized polymer described herein can form a layer of coating on a stent. The layer of coating can be thin, e.g., in the 2 to 3 micron range. In some embodiments, where the coating includes a bioactive agent such as everolimus, the PC functionalized polymer can be applied as a thin topcoat on a controlled release aliphatic matrix layer (e.g., a PE matrix layer) that contains the bioactive agent. This PE layer would have the same composition as the PE that is functionalized with PC so as to achieve interfacial compatibility. The PE polymer in the matrix layer and the PE polymer functionalized by PC can be same or different. The construct can include a layer of 2 to 3 micron that provides for control of the release of drug followed by a PC functionalized PE topcoat of 1 to 2 micron.

In some embodiments, alternatively, a layer of pure-drug can be sandwiched between a primer layer or a bare metal stent surface and a PC functionalized PE topcoat of 1 to 2 micron.

In some embodiments, any of the coating constructs described above can be formed on top of a bare metal stent (BMS) scaffold or an absorbable scaffold of stent.

Bioactive Agents

In some embodiments, a coating that includes a PC functionalized polymer described herein can optionally include one or more bioactive agents. These bioactive agents can be any agent which is a therapeutic, prophylactic, or diagnostic agent. These agents can have anti-proliferative or anti-inflammatory properties or can have other properties such as anti-neoplastic, antiplatelet, anti-coagulant, anti-fibrin, antithrombotic, antimitotic, antibiotic, antiallergic, or antioxidant properties. Moreover, these agents can be cystostatic agents, agents that promote the healing of the endothelium, or agents that promote the attachment, migration and proliferation of endothelial cells while quenching smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules, which bind to complementary DNA to inhibit transcription, and ribozymes. Some other examples of bioactive agents include antibodies, receptor ligands, enzymes, adhesion peptides, blood clotting factors, inhibitors or clot dissolving agents, such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxyl)ethyl-rapamycin (everolimus), and its functional or structural derivatives, paclitaxel and its functional and structural derivatives. Examples of rapamycin derivatives include ABT-578, 40-O-(3-hydroxyl)propyl-rapamycin, 40-O-[2-(2-hydroxyl)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax™ (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include biolimus, tacrolimus, dexamethasone, dexamethasone derivatives, mometasone, mometasone derivatives, clobetasol, other corticosteroids or combinations thereof. Examples of such cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, and genetically engineered epithelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

In some embodiments, a coating including a polymer(s) described herein can specifically exclude any one or more of the above described agents.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by those of ordinary skill in the art.

Examples of Medical Devices

As used herein, a medical device may be any suitable medical substrate that can be implanted in a human or veterinary patient. Examples of such medical devices include self-expandable stents, balloon-expandable stents, stent-grafts, grafts (e.g., aortic grafts), heart valve prostheses, cerebrospinal fluid shunts, pacemaker electrodes, catheters, and endocardial leads (e.g., FINELINE® and ENDOTAK®, available from Guidant Corporation, Santa Clara, Calif.), anastomotic devices and connectors, orthopedic implants such as screws, spinal implants, and electro-stimulatory devices. The underlying structure of the device can be of virtually any design. The device can be made of a metallic material or an alloy such as, but not limited to, cobalt chromium alloy (ELGILOY®), stainless steel (316L), high nitrogen stainless steel, e.g., BIODUR® 108, cobalt chrome alloy L-605, "MP35N," "MP20N," ELASTINITE® (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable (e.g., bioabsorbable stent) or biostable polymers could also be used with the embodiments of the present invention.

Method of Use

Preferably, the medical device is a stent. The stent described herein is useful for a variety of medical procedures, including, by way of example, treatment of obstructions caused by tumors in bile ducts, esophagus, trachea/bronchi and other biological passageways. A stent having the above-described coating is particularly useful for treating diseased regions of blood vessels caused by lipid deposition, monocyte or macrophage infiltration, or dysfunctional endothelium or a combination thereof, or occluded regions of blood vessels caused by abnormal or inappropriate migration and proliferation of smooth muscle cells, thrombosis, and restenosis.

Stents may be placed in a wide array of blood vessels, both arteries and veins. Representative examples of sites include the iliac, renal, carotid and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter that allows a stent in its collapsed configuration to be inserted into the passageway. The delivery catheter is inserted either percutaneously or by surgery into the femoral artery, radial artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

The implantable device can be implanted in any mammal, e.g., an animal or a human being. In some embodiments, the implantable device can be implanted in a patient in need of treatment by the implantable device. The treatment can be angioplasty or other type of treatments involving an implantable device.

A patient who receives the implantable device described herein can be male or female under normal body condition (e.g., normal weight) or abnormal body condition (e.g., underweight or overweight). The patient can be in any age, preferably, the patient is in an age ranging from about 40 to 70 years. An index for measuring the body condition of a patient is BMI (body mass index). A patient can have a BMI ranging from about 18 to about 30 or above.

The implantable device described herein can be used to treat or ameliorate a medical condition such as atherosclerosis, thrombosis, restenosis, hemorrhage, vascular dissection or perforation, vascular aneurysm, vulnerable plaque, chronic total occlusion, claudication, type-II diabetes, anastomotic proliferation for vein and artificial grafts, bile duct obstruction, ureter obstruction, tumor obstruction, or combinations thereof.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

We claim:

1. A coating on a medical device, comprising a phosphorylcholine (PC) functionalized aliphatic absorbable polymer; wherein the aliphatic absorbable polymer comprises poly glycerol sebacate.

2. The coating of claim 1, wherein the PC functionalized aliphatic polymer forms a thin topcoat on top of a matrix layer comprising a polyester and a bioactive agent.

3. The coating of claim 1, wherein the PC functionalized aliphatic polymer forms a thin topcoat on top of a pure drug layer that is formed on a primer layer or a medical device surface.

4. The coating of claim 1, formed on a bare metal stent or an absorbable stent.

5. The coating of claim 1, further comprising a bioactive agent.

6. The coating of claim 5, wherein the bioactive agent is paclitaxel, docetaxel, estradiol, 17-beta-estradiol, a nitric oxide donor, a super oxide dismutase, a super oxide dismutase mimic, 4-amino-2,2,6,6-tetramethylpiperidine-1-oxyl (4-amino-TEMPO), tacrolimus, dexamethasone, dexamethasone acetate, rapamycin, a rapamycin derivative, 40-O-(2-hydroxyl)ethyl-rapamycin (everolimus), 40-O-(3-hydroxyl)propyl-rapamycin, 40-O-[2-(2-hydroxyl)ethoxy]ethyl-rapamycin, 40-O-tetrazole-rapamycin, 40-epi-(N1-tetrazolyl)-rapamycin (ABT-578), γ-hiridun, clobetasol, mometasone, pimecrolimus, imatinib mesylate, midostaurin, or a prodrug of these, a co-drug of these, or a combination of these.

7. The coating of claim 1, wherein the medical device is a stent.

8. The coating of claim 1, wherein the medical device is a bioabsorbable stent.

9. The coating of claim 1, wherein the PC functionalized aliphatic absorbable polymer comprises at least one PC moiety within the backbone of the polymer or as a pendant group off the polymer backbone.

10. A method of treating or ameliorating a medical condition in a patient, comprising implanting in the patient a medical device comprising the coating according to claim 1.

11. A method of treating or ameliorating a medical condition in a patient, comprising implanting in the patient a medical device comprising the coating according to claim 6.

12. The coating of claim 5, wherein the bioactive agent is paclitaxel, docetaxel, estradiol, 17-beta-estradiol, a nitric oxide donor, a super oxide dismutase, 4-amino-2,2,6,6-tetramethylpiperidine-1-oxyl (4-amino-TEMPO), tacrolimus, dexamethasone, dexamethasone acetate, rapamycin, 40-O-(2-hydroxyl)ethyl-rapamycin (everolimus), 40-O-(3-hydroxy)-propyl-rapamycin, 40-O-[2-(2-hydroxyl)ethoxy]ethyl-rapamycin, 40-O-tetrazole-rapamycin, 40-epi-(N1-tetrazolyl)-rapamycin (ABT-578), γ-hiridun, clobetasol, mometasone, pimecrolimus, imatinib mesylate, midostaurin, or a combination of these.

13. A method of treating or ameliorating a medical condition in a patient, comprising implanting in the patient a medical device comprising the coating according to claim 12.

14. A medical device comprising the coating according to claim 1.

15. A medical device comprising the coating according to claim 2.

16. A medical device comprising the coating according to claim 3.

17. A medical device comprising the coating according to claim 4.

18. A medical device comprising the coating according to claim 5.

19. A medical device comprising the coating according to claim 6.

20. A medical device comprising the coating according to claim 12.

21. The coating of claim 2, wherein the polyester of the matrix layer is the same polymer as the aliphatic polymer functionalized with PC of the topcoat.

22. The coating of claim 2, wherein the polyester of the matrix layer is a different polymer than the aliphatic polymer functionalized with PC of the topcoat.

23. The coating of claim 3, wherein the medical device is a metal stent, and the pure drug layer is formed on the surface of the stent.

24. The coating of claim 3, wherein the medical device is an absorbable stent, and the pure drug layer is formed on the surface of the stent.

* * * * *